(12) United States Patent
Williamson

(10) Patent No.: US 12,243,061 B1
(45) Date of Patent: Mar. 4, 2025

(54) REAL-TIME CONTAGION MONITORING AND PREVENTION MECHANISM FOR DEMONSTRATING CONTAGION-RELATED COMPLIANCE

(71) Applicant: Susan Elaine Williamson, Oakland Park, FL (US)

(72) Inventor: Susan Elaine Williamson, Oakland Park, FL (US)

( * ) Notice: Subject to any disclaimer, the term of this patent is extended or adjusted under 35 U.S.C. 154(b) by 264 days.

(21) Appl. No.: 17/703,324

(22) Filed: Mar. 24, 2022

Related U.S. Application Data

(63) Continuation-in-part of application No. 16/702,418, filed on Dec. 3, 2019, now abandoned, which is a continuation-in-part of application No. 15/455,056, filed on Mar. 9, 2017, now Pat. No. 10,521,752.

(60) Provisional application No. 62/305,702, filed on Mar. 9, 2016.

(51) Int. Cl.
  *G06Q 30/018* (2023.01)
  *G16H 40/63* (2018.01)

(52) U.S. Cl.
  CPC ........... *G06Q 30/018* (2013.01); *G16H 40/63* (2018.01)

(58) Field of Classification Search
  CPC ............................ G06Q 30/018; G16H 40/63
  See application file for complete search history.

(56) References Cited

U.S. PATENT DOCUMENTS

| | | | |
|---|---|---|---|
| 8,712,813 B2 * | 4/2014 | King | G06Q 10/0639 705/7.29 |
| 2020/0176125 A1 * | 6/2020 | Chatterjea | G06K 7/10366 |
| 2021/0390807 A1 * | 12/2021 | Chaurasia | G07C 9/27 |
| 2022/0359086 A1 * | 11/2022 | Correnti | G16H 50/30 |

\* cited by examiner

*Primary Examiner* — Brian Wilson
(74) *Attorney, Agent, or Firm* — John Rizvi; John Rizvi, P.A.—The Patent Professor®

(57) ABSTRACT

A mechanism for implementing and demonstrating compliance with contagion-related protocols, the mechanism comprising, a temperature screening and monitoring sub-mechanism, a proximity screening and monitoring sub-mechanism, and a contact tracing sub-mechanism. Personal proximity beacons monitor distances between individuals to ultimately provide alerts. A dashboard allows for real-time monitoring and compliance demonstrating. Mask wearing and body temperature is monitored via surveillance cameras (traditional and thermal).

1 Claim, 11 Drawing Sheets

REAL-TIME CONTAGION MONITORING AND PREVENTION MECHANISM FOR DEMONSTRATING CONTAGION-RELATED COMPLIANCE

CROSS-REFERENCE TO RELATED APPLICATION

This application claims the benefit of co-pending Non-Provisional patent application Ser. No. 16/702,418 filed Dec. 3, 2019 which is a Continuation-in-Part claiming the benefit of co-pending Non-Provisional patent application Ser. No. 15/455,056, filed Mar. 9, 2017, which in turn claims priority to Provisional Patent Application No. 62/305,702 filed Mar. 9, 2016 which are all incorporated herein in their entireties.

FIELD OF THE INVENTION

The present invention relates generally to health & safety protocols and more particularly, to a monitoring and prevention mechanism for demonstrating contagion-related compliance.

BACKGROUND OF THE INVENTION

Contagious diseases are a well-known threat to human health and safety. For example, COVID-19 is a disease caused by the extremely contagious SARS-CoV-2 coronavirus. Some contagious diseases are not dangerous while others can be extremely dangerous, and some can be very contagious and some can be less contagious. Diseases that are characterized as "very contagious, very dangerous", such as COVID-19, are of particular concern to governments, businesses, and organizations.

Typically, governments and international agencies are involved in controlling, monitoring, and managing contagious diseases. For example, the Centers for Disease Control and Prevention (CDC) [USA] or the World Health Organization (WHO) [International] are such agencies. These agencies can directly or indirectly influence the rules that individuals and businesses are required to follow for health & safety compliance.

The cruise industry and other travel industries are heavily dependent on such regulations because of the nature of their services. For example, cruise liners rely on transporting a significant number of individuals in close proximity and the passengers are typically encouraged to mingle freely through various locations and services offered on a ship (e.g. bars, restaurants, entertainment venues, etc.)

In response to infectious diseases, such as COVID-19 as well as other infectious viruses such as Norovirus, authorities have required cruise liners to follow rigorous methods for business to continue. More particularly, with respect to COVID-19, the CDC requires cruises to be able to comprehensively demonstrate the ability to detect, prevent, and provide care for infectious diseases especially COVID-19. Among various metrics, the CDC cares about social distancing, mask wearing, hand hygiene, and sanitation.

However, currently there are no existing solutions to demonstrate such ability in a comprehensive, real-time, and effective manner that can be trusted by the CDC or other global health authorities. For example, temperature screenings are typically done before allowing individuals to enter establishments or cruises, but this alone is not good enough. The distance between individuals and their identities, among other parameters, need to be tracked in real time and compiled to identify transmission risk events. But there currently is no solution that comprehensively tracks and monitors all risk parameters, at once, in a real-time fashion so that a potential outbreak can be detected and controlled before it occurs.

Therefore, there exists a need for a monitoring and prevention mechanism for demonstrating contagion-related compliance in a comprehensive, effective, transparent, and trustworthy manner.

SUMMARY OF THE INVENTION

This summary is provided to introduce a selection of concepts in a simplified form that are further described below in the detailed description. This summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Disclosed herein is a mechanism for implementing and demonstrating compliance with contagion-related protocols, the mechanism comprising, a temperature screening and monitoring sub-mechanism, a proximity screening and monitoring sub-mechanism, and a contact tracing sub-mechanism.

In one aspect, the temperature screening and monitoring sub-mechanism includes a temperature reading of an individual.

In another aspect, the temperature screening and monitoring sub-mechanism includes a thermal camera.

In another aspect, the proximity screening and monitoring sub-mechanism includes a wearable proximity beacon.

In another aspect, the proximity screening and monitoring sub-mechanism includes one or more cameras.

In another aspect, the contact tracing sub-mechanism relates two data points, where a first data point of the two data points relates to one individual in possible transmission risk, and the second data point of the two data points relates to a second individual that is determined to be in contact with the first individual.

In another aspect, the proximity screening and monitoring sub-mechanism includes a body counter that is configured to automatically count individuals entering or located within a specific area.

In another aspect, the contact tracing sub-mechanism includes a machine-readable code that is scannable to determine a sequence of identities within a queue.

In another aspect, the contact tracing sub-mechanism includes a wearable device that is scannable to determine a sequence of identities within a queue.

In another aspect, the mechanism comprises a processor configured for communicating compliance data through a dashboard, wherein the dashboard is configured to receive a plurality of data streams relating to various contagion-related risk parameters, wherein the data streams include at least one data stream relating to social distancing, wherein the data streams include at least one data stream relating to hand hygiene, wherein the data streams include at least one data stream relating to surface sanitization, wherein the data streams include at least one data stream relating to face mask wearing, wherein the data streams include at least one data stream relating to air quality, wherein the data streams include at least one data stream relating to body temperature, wherein the data streams include at least one data stream relating to body count in an area, wherein the mechanism automatically identifies individuals by detecting a signature, wherein the signature is at least one of a biological signature, facial recognition signature, a QR Code, a text code, and an RFID wearable, and wherein the mechanism automatically tracks mask wearing and determines if masks are worn correctly. These data streams can be represented either collectively or individually through a dashboard that is updated in real time, allowing a user to determine compliance.

In another aspect, the mechanism automatically determines if a hand hygiene apparatus has been activated, the hygiene apparatus being at least one of a sink and a hand sanitizer station.

In another aspect, the mechanism automatically determines if a hand hygiene routine is executed properly by detecting the use of soap and/or hand sanitizer.

In another aspect, the mechanism automatically determines if a surface cleaning routine has been executed properly by checking the presence of an identifier residue.

In another aspect, the mechanism automatically determines a number of people entering a specific area via scanning a machine-readable code and/or wireless beacon.

In another aspect, the mechanism automatically determines if a social distancing threshold has been broken by monitoring distances between two or more proximity beacons worn by individuals.

In another aspect, the mechanism receives and processes information from one or more auditing systems for creating audits and capturing data via created audits, wherein an auditing system is defined as having, one or more storage machines holding instructions executable by one or more logic machines to effect the operations of, creating an audit, presenting the audit to an auditor user, capturing data via an interface of the audit, compiling the data as results, presenting the results, wherein the audit includes audit elements, the audit elements configured to generate a score, wherein the instructions are further executable to categorize generated scores, and wherein the instructions are further executable to determine a location of an auditor device for sending audit content to the auditor device according to the location.

In another aspect, the mechanism receives and processes information from an auditing and performance driving system, wherein the system is defined as having, one or more storage machines holding instructions executable by one or more logic machines to effect the operations of, from a group of tasks provided by upper management, schedule tasks according to a unique time schedule of an individual facility while obeying restrictions applied by the upper management, delegate one or more of the tasks to one or more employees, to an assignee employee, display one or more steps required to complete the delegated task, receiving an input that indicates that an employee has completed a delegated task, creating an audit for auditing the task, presenting the audit to an auditor user, capturing data via an interface of the audit, compiling the data as results, and presenting the results.

In another aspect, the mechanism is configured to display a dashboard that is updated in real time, according to real-time-updated data streams of various parameters.

In another aspect, the mechanism is configured to generate a compliance reading in response to analyzing a plurality of contagion-related parameters continuously updated in real-time.

Furthermore, disclosed is a mechanism for implementing and demonstrating compliance with contagion-related protocols, the mechanism comprising a processor configured for communicating compliance data through a dashboard, wherein the dashboard is configured to receive a plurality of data streams relating to various contagion-related risk parameters, wherein the mechanism is configured to store and/or access personal details of a passenger, the details being at least one of personal ID info, health info, passport pages, and travel history, wherein the mechanism is configured to read QR codes to determine a volume of people, a sequence/distance between people, execute contact tracing based on a position in queue, and track passenger progress through busses & terminals, wherein the mechanism is configured to execute temperature screening and associate the temperature with a passenger name/ID, passenger temperature, crew name/ID, and crew temperature, wherein the mechanism is configured to keep track of staff ID #, staff name, department, when an area is cleaned, a name/ID of cleaner, an area and sub-area, whether PPE was worn, PPM chemicals detected, whether a sanitizing technique was conducted, the results or execution of swab tests, and the execution and/or results of a gel test, wherein the mechanism is configured to gather information from personal proximity beacons and associate such beacons with a passenger name/ID, their area/location, a crew name/ID and/or their location, wherein the mechanism is configured to execute contact tracing by determining a passenger name/ID, their area/location, the contacts they have had (e.g. passenger/crew), the crew or passenger name in contact, wherein relationships between the one or more data streams, or data stores, are evaluated to determine a level of compliance, represented by one or more numbers or visual representations, or semantic or haptic representations, wherein data is reported in true real-time, updated continuously, driving the ability for immediate corrective action, wherein data is reported to indicate compliance with standards, reporting at least a percentage of individuals wearing masks, wherein particulate matter below a threshold is detected using an air quality sensor, wherein the mechanism automatically schedules next actions according to a detected contagion-related risk condition, including at least a nearest worker being assigned to investigate improper mask wearing or being assigned to sanitize a surface, wherein a QR code portion triggers and records each step of an individual through an onboarding process, wherein a proximity technology monitors distances between individuals, tracks and communicates resulting data, and communicates alarms in response to threshold distances being breached or a threshold number of individuals being detected in a certain area, wherein IoT sensors are deployed in health & safety appliances, wherein body volume is determined by automatically tracking a number of QR reads, proximity beacon reads, surveillance camera reads, and people counting devices, wherein relationships between the beacon and mask wearing is determined, the beacons recording encounters and the unique IDs of all individuals, for tracing contacts, a position in a queue is determined via QR code scanning to track down people who might have been infected, wherein the proximity beacons are used for tracing contacts by flagging contacts who have reached a certain proximity with an individual or user, wherein the beacons are used for people counting and surveillance cameras are used for tracing contacts as well as identifying the IDs of individuals and identify people who are not wearing masks, wherein for temperature screening, data from a hand-held gun or touchless automatic temperature screener are fed into a data stream, wherein a go/stop signal indicates whether the individual is allowed to proceed passed the checkpoint, wherein two or more cameras are simultaneously paired to determine temperature, including a thermal imaging camera and a regular surveillance camera, wherein a venue or transit area includes a BG/R Bluetooth Gateway or reader which is configured to communicate with a personal proximity beacon to determine the proximity of passengers in a specific area and to count individuals and wherein a volume-control display communicates whether it is OK to enter or when it is not OK to enter according to volume/proximity thresholds.

It is to be understood that "Passenger", as used above or below, could also be (or include) crew, customers, workers, employees, and patrons. Where QR codes are mentioned, RFID could be used alternatively or additionally.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
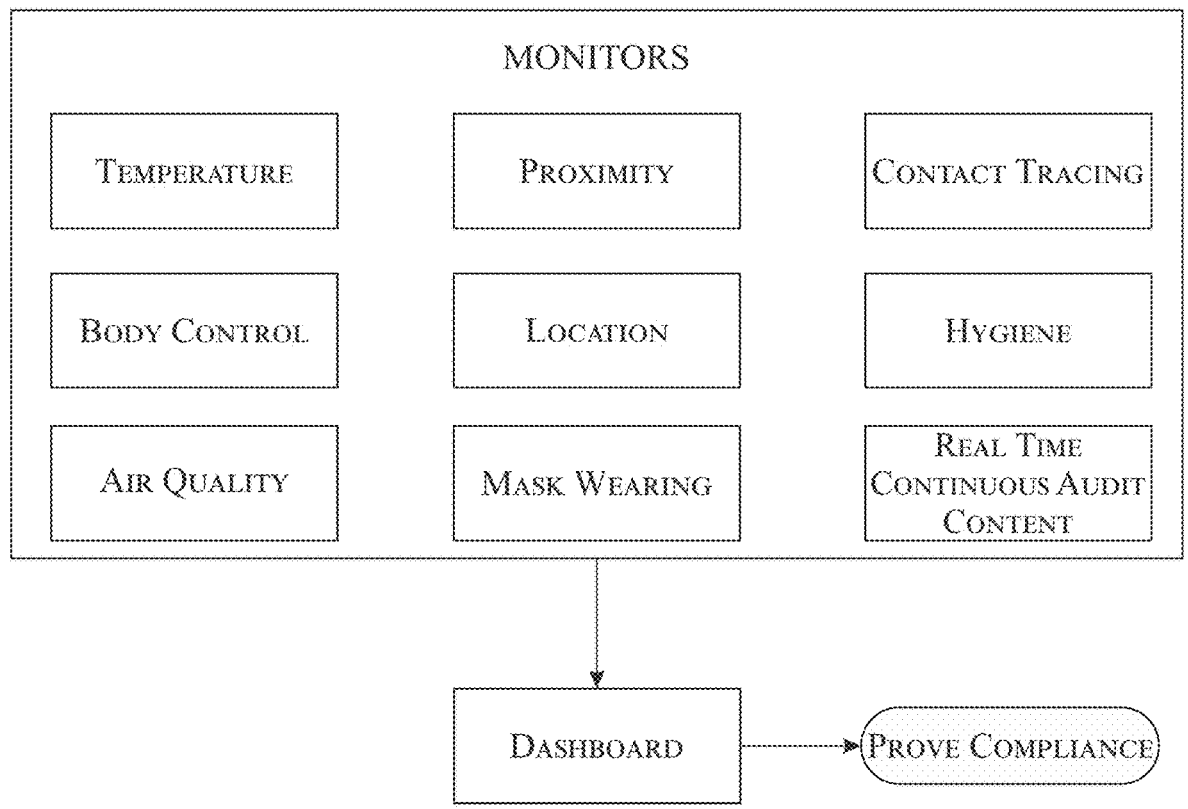
FIG. 1 schematically presents one or more monitors configured for collecting and relaying information to a dashboard with the objective to demonstrate compliance using systematically and/or automatically collected data, in accordance with aspects of the present disclosure.
Figure 2:
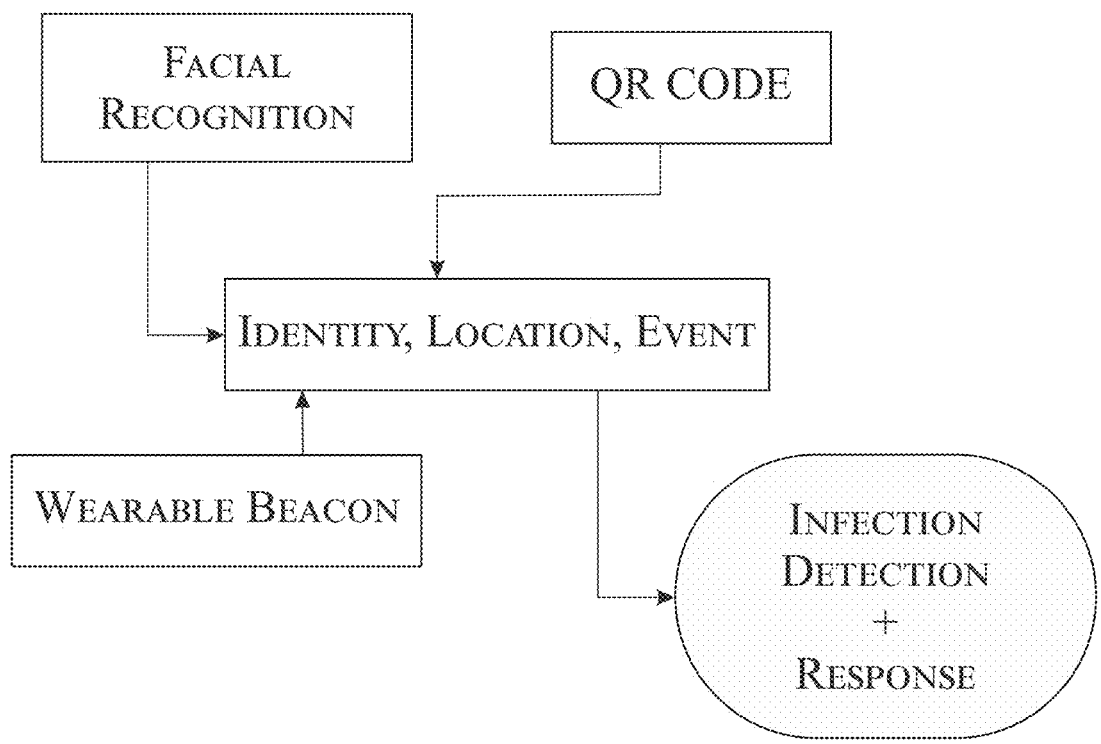
FIG. 2 schematically presents a subsystem where identity, location, or event detection is supported by data received from facial recognition, QR code, wearable beacons, or other specially configured data sources, to effect infection detection and response thereto, in accordance with aspects of the present disclosure.
Figure 3:
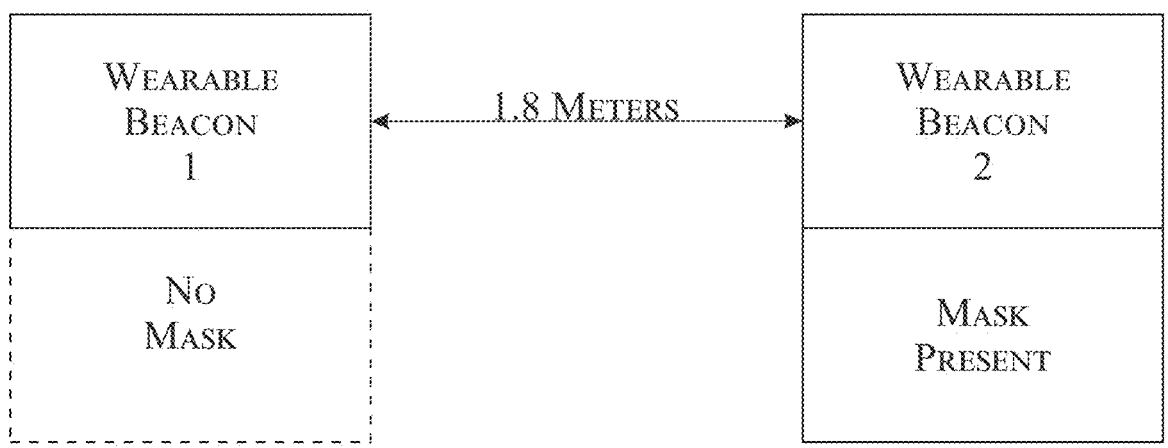
FIG. 3 schematically presents an "indoor hallway" scenario where two beacons have reached a threshold proximity distance, and where mask wearing has a first permutation (e.g. one person with no mask, another person with a mask). In this figure an alert condition is detected, in accordance with aspects of the present disclosure.
Figure 4:
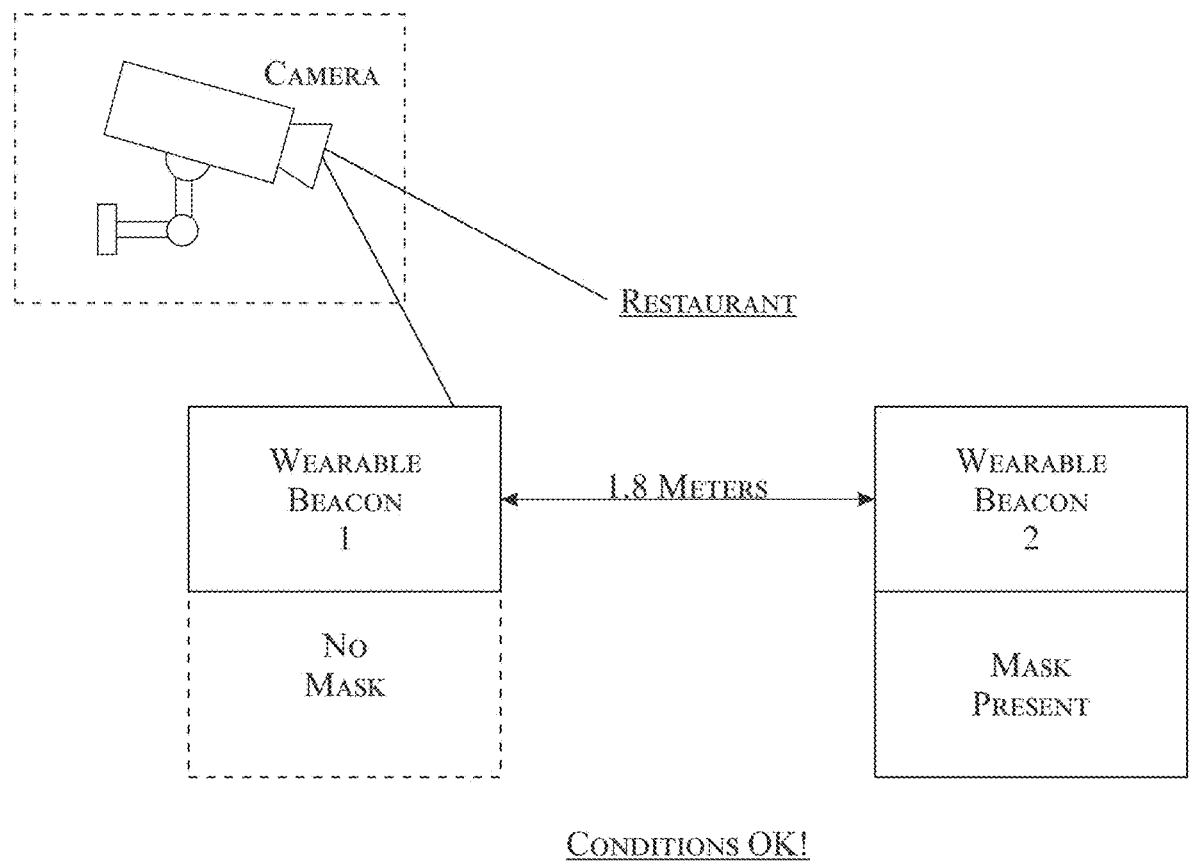
FIG. 4 schematically presents a "restaurant" example where the mask wearing permutation includes one person not wearing a mask and a second person wearing a mask. Knowing the situation (e.g restaurant) the system determines conditions as "OK" because this arrangement has been deemed allowable in a restaurant, in accordance with aspects of the present disclosure, FIG. 5 schematically presents an example venue entrance where occupancy (or vacancy) is shown along with a "stop" and "go" signal while remaining within compliance of social distancing requirements, in accordance with aspects of the present disclosure.
Figure 5:
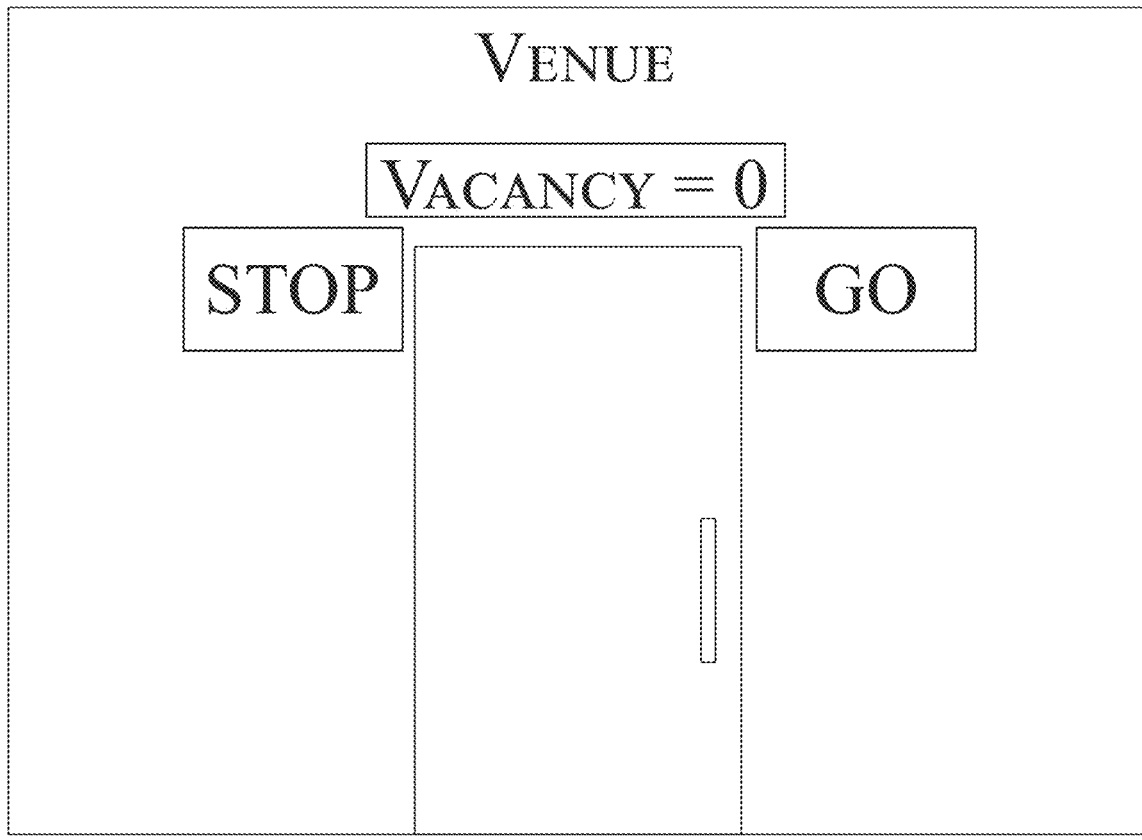
Figure 6:
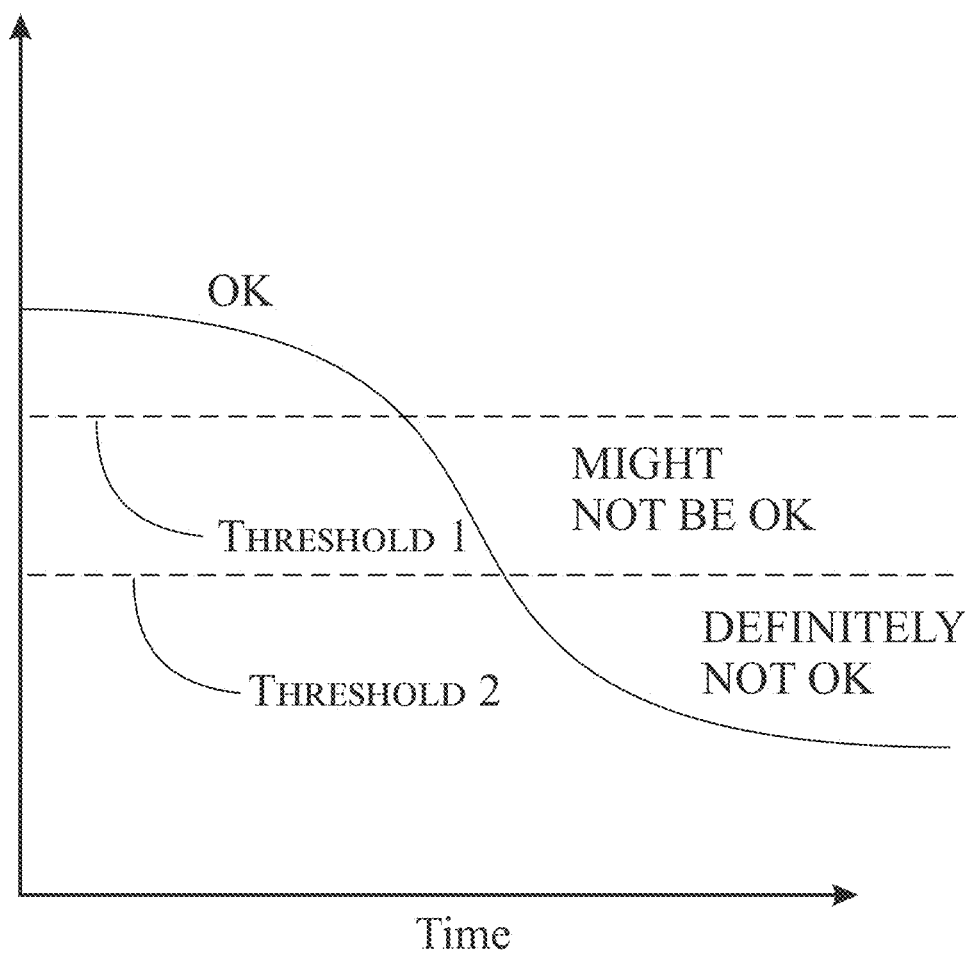
FIG. 6 schematically presents an example graph which highlights a threshold compliance number, which could be threshold values set for various parameters viewable through a dashboard for example, and where the compliance number threshold can be broken to create an alert message "Not OK". There may be several thresholds such as a "something might not be OK", or a caution zone, or any number of thresholds to represent levels or zones of non-compliance or compliance.
Figure 7:
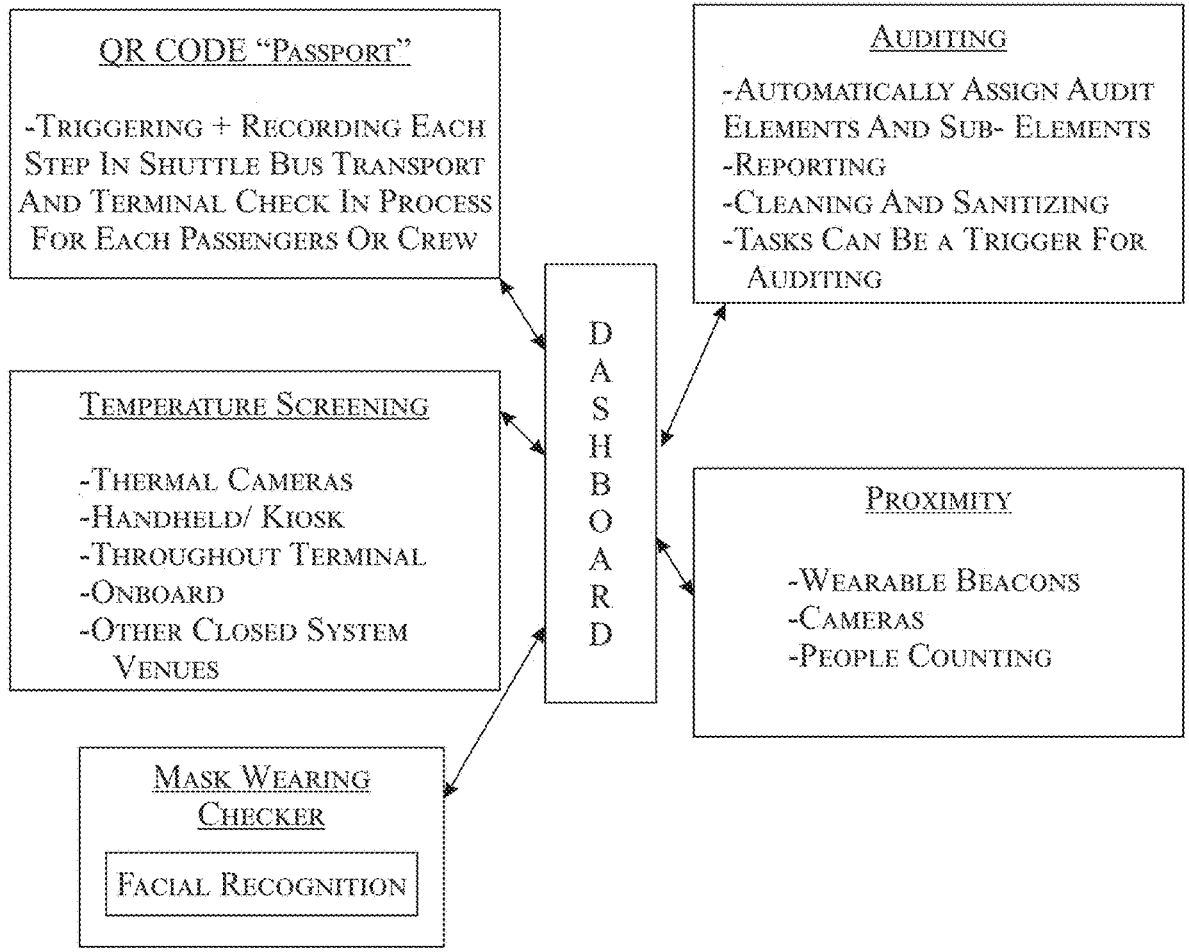
FIG. 7 schematically presents an example overview of how various inputs gather information into the dashboard. For example a QR Code scan location, data gatherers for temperature screening, mask wearing checker, auditing system, and proximity detectors can gather and submit information into the dashboard for display and processing (e.g. alerts, messages, reports, etc.)
Figure 8:
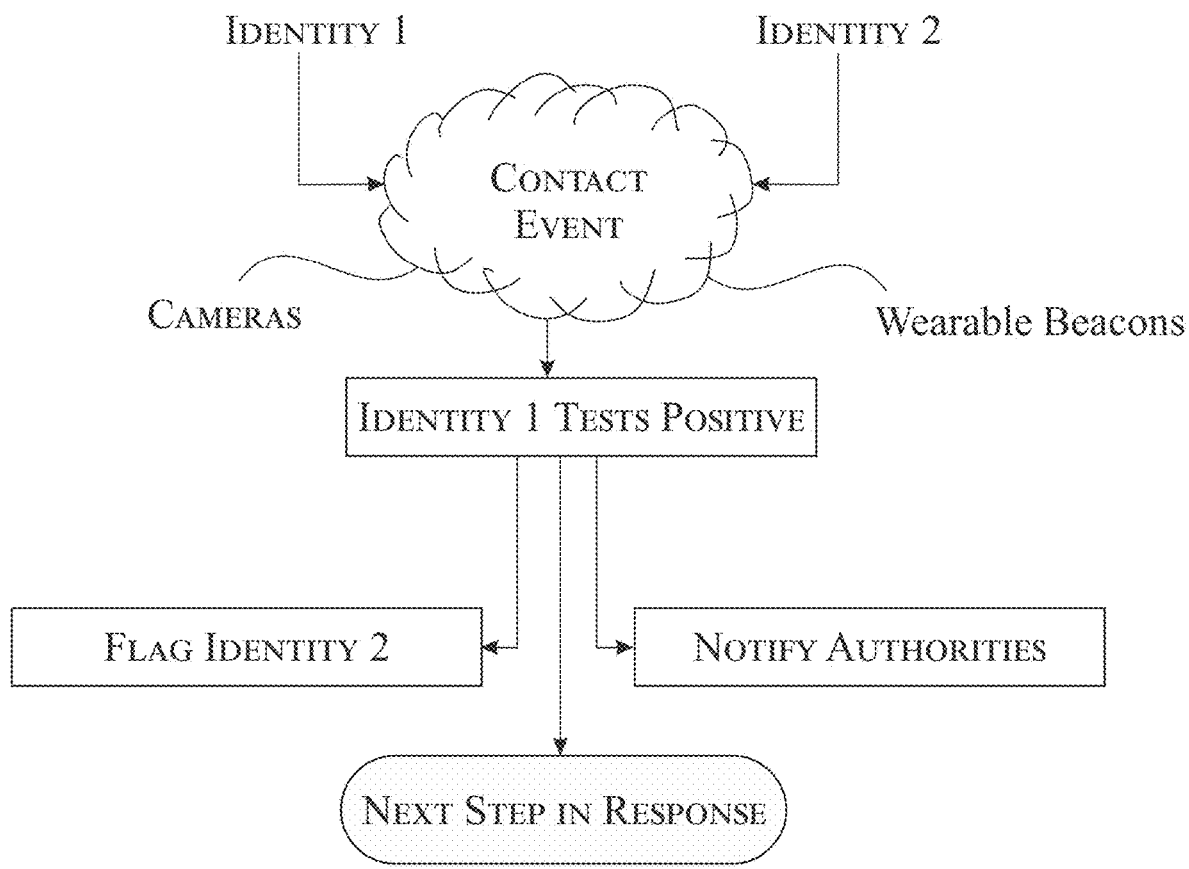
FIG. 8 schematically presents an example contact tracing and response method, where one past contact identity is flagged based on a future positive test, in accordance with aspects of the present disclosure.
Figure 9:
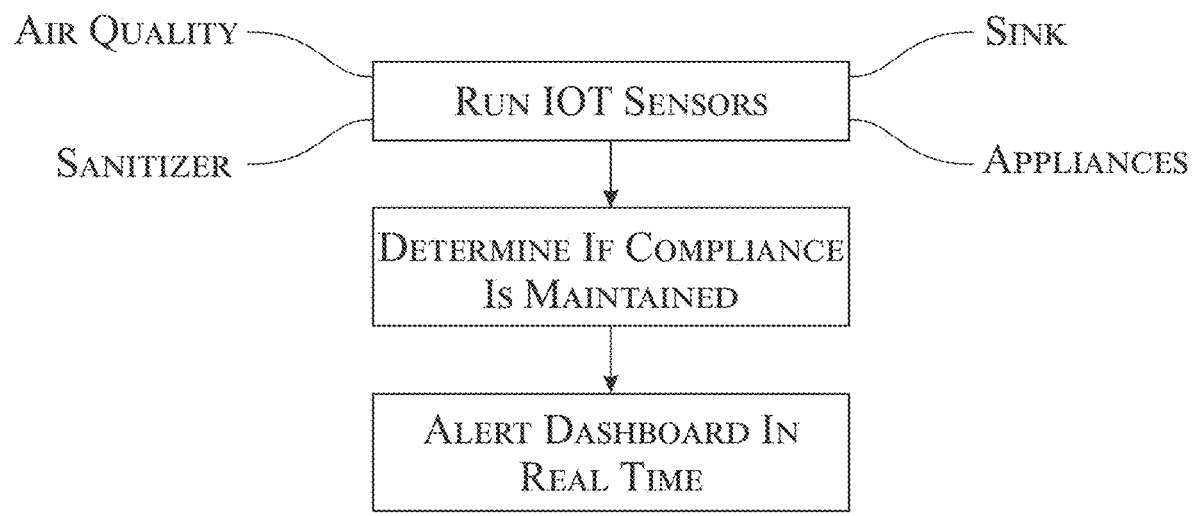
FIG. 9 schematically presents an example method where air quality devices and appliances include IoT sensors to determine if compliance is maintained and furthermore subsequently alert a dashboard in real time, in accordance with aspects of the present disclosure.
Figure 10:
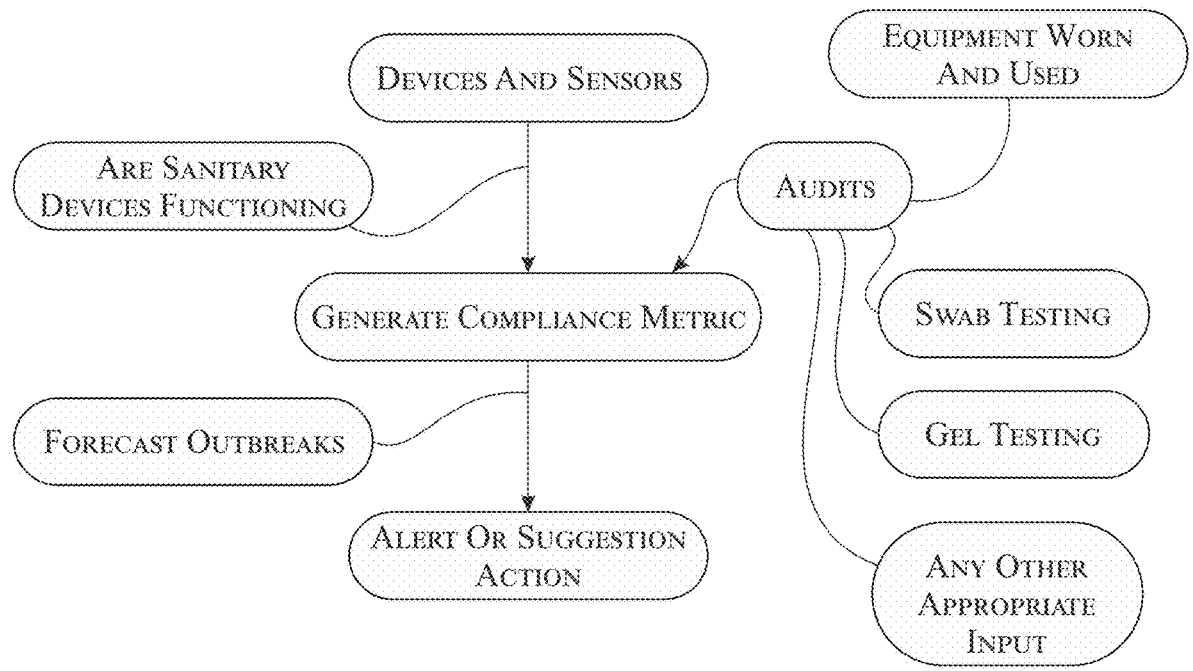
FIG. 10 schematically presents devices and sensors being an input for processors to generate compliance metrics, and create an alert or suggested action, in accordance with aspects of the present disclosure.
Figure 11:
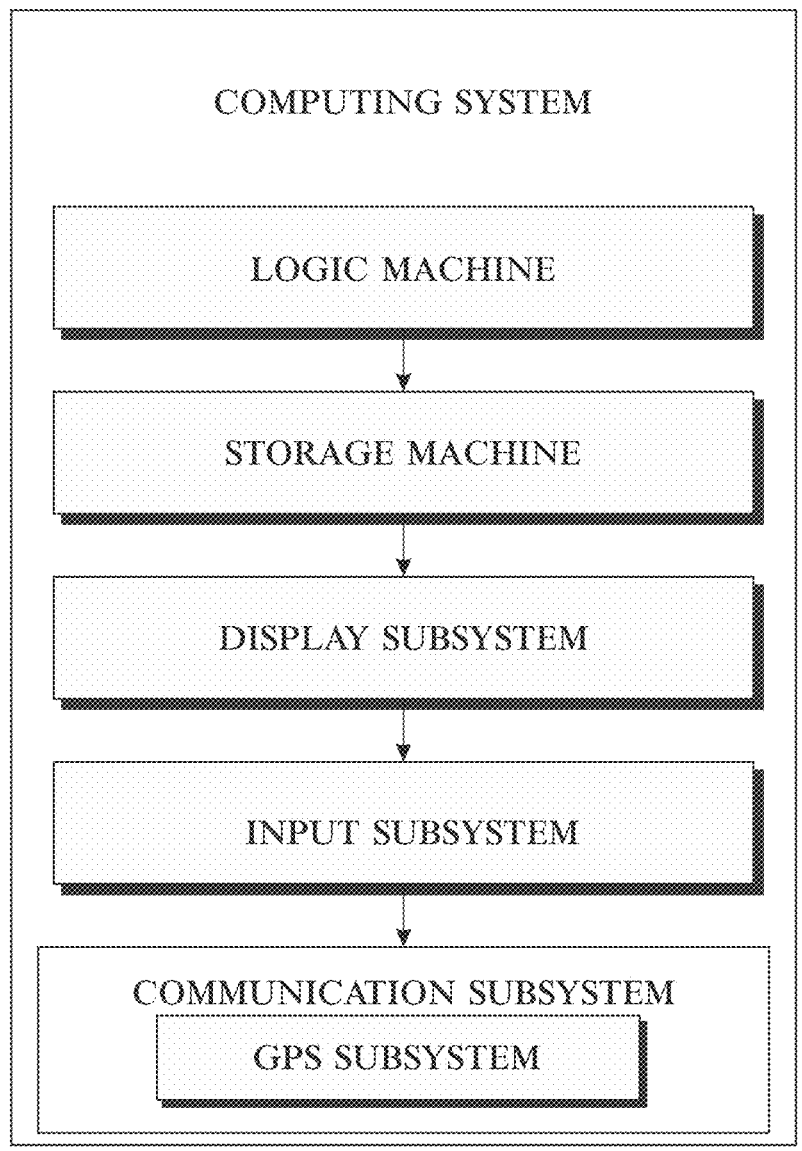
FIG. 11 schematically presents an example computing system that can be an essential part of the disclosed method, in accordance with aspects of the present disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Disclosed is a real-time monitoring and prevention mechanism for demonstrating contagion-related compliance. The mechanism may include one or more storage machines holding instructions executable by one or more logic machines to execute various operations. The mechanism could be employed in/for physical spaces of various businesses, organizations, or entities.

The mechanism may include the ability to communicate compliance data through a dashboard, wherein the dashboard is configured to receive a plurality of data streams relating to various contagion-related risk parameters. For example, by looking at the dashboard, a user could determine if their cruise ship is operating with sufficient compliance. The plurality of data streams could include at least one data stream relating to social distancing (i.e. social distancing data). This will aid in remaining in compliance with social distancing requirements. Such requirements may be dynamic depending on situation (e.g. both people wearing masks vs only one person wearing a mask). This is further described below.

The plurality of data streams may include at least one data stream relating to hand hygiene (i.e. hand hygiene data). This data could be used in the dashboard to determine if an individual or group of individuals have used a hand hygiene appliance properly. For example, one individual could be identified as not having used soap, or having not washed their hands long enough.

The plurality of data streams could include at least one data stream relating to surface sanitizing and/or cleaning (i.e. surface sanitizing data). This is further described below. For example, various swab or gel tests could be used to determine the cleanliness of a surface, or to determine if a surface has been sanitized or cleaned. This data could be fed into the system to determine compliance on an overall scale, but it is to be understood that the system allow for an extremely narrow determination, by finding out exactly to which extent a specific worker has sanitized a surface (e.g. using the audit system mentioned herein).

The plurality of data streams may include at least one data stream relating to face mask wearing (i.e. mask wearing data). For example, individuals not wearing masks can be detected as an event and their identities could be reported for investigation. This can be done via any appropriate method, such as facial recognition, biometric recognition, or voice recognition, as non-limiting examples.

The plurality of data streams may include at least one data stream relating to air quality (i.e. air quality data). For example, IoT sensors could be deployed in various airflow systems to determine if dangerous particular matter is present (e.g. a virus). Such information could be fed into the system to have a real-time stream of safety compliance. For example, upon detecting that air quality is dangerous (i.e. detecting a virus) the system could display an alert or send a message to an authority. In another example, particulate matter on the order of PM2.5 (e.g. below 2.5 microns) is detected using the air quality sensor. In another example, particles under 0.06 to 0.14 microns are detected. In another example, IoT sensors are deployed in various health & safety appliances such as hand sanitizers, air conditioning systems, sinks, and deployed in doorways to detect a volume flow of individuals.

The plurality of data streams may include at least one data stream relating to body temperature (i.e. body temperature data). For example, for temperature screening, data from a hand-held gun or touch-less automatic temperature screener could be fed into a data stream. For example staff could scan a QR code and read a temperature with a temperature gun to simultaneously record a date/time, temperature, location, and identity of the scanned individual. A go/stop signal could indicate whether the individual is allowed to proceed passed the checkpoint. Such process could also be done at a temperature-reading kiosk. For example, stop and go devices are located outside rooms or venues that indicate when individuals are allowed to enter (go) or when individuals are required to wait (stop), according to volume threshold requirements determined by the system.

Two or more cameras can be simultaneously paired to determine temperature, such as a thermal imaging camera and a regular surveillance camera. Such body temperature readings could be used to determine a final outcome of a data stream (e.g. body temperature readings are within acceptable levels), or a percentage of population having healthy body temperatures could be determined and displayed in the dashboard. The mechanism is configured to execute temperature screening and associate the temperature with a passenger name/ID, passenger temperature, crew name/ID, and crew temperature.

The plurality of data streams may include at least one data stream relating to coughing frequency or intensity (i.e. coughing data). The coughing data could be generated in response to monitoring gestures or sounds. Sneezing could also be monitored through gesture or audio monitoring.

The plurality of data streams may include at least one data stream relating to body count in an area (i.e. body count data, volume, body density). Bodies can be counted via various systems such as thermal cameras, traditional cameras, 3D cameras, or by the employment of gateways that detect wireless communication wearables (e.g. beacons). For example, the mechanism automatically identifies individuals by recording or detecting a signature (e.g. biological signature, facial recognition, QR Code, text code, RFID wearable, etc.) IoT masks can be used for any of these purposes.

The mechanism may automatically track mask wearing and determine if masks are worn correctly. This can be done using an artificial intelligence algorithm that visually determines the absence or presence of a mask. Other systems and methods are anticipated, such as the use of IoT masks that determine proper donning of the mask via sensors (e.g. force sensors).

The mechanism may automatically determine if a hand hygiene apparatus has been activated (e.g. used properly), such as a sink, or a hand sanitizer station. This can be done by including sensors in the apparatuses such as flow sensors, or motions sensors. But in some examples this can be done using surveillance cameras and wearable beacon detectors. In this way, the mechanism automatically determines if a hand hygiene routine is executed properly (e.g. by detecting the use of soap and/or hand sanitizer.) This mechanism could also determine a duration of activity at a sink (e.g. how long hands are washed for.)

The mechanism may automatically determine if a surface cleaning routine has been executed properly (e.g. by checking the presence of an identifying residue.) This can be done with swab or gel tests, or any appropriate method. Visual tests can be done using specially configured light.

The mechanism may automatically determine a number of people entering a specific area (e.g. via scanning a machine-readable code, QR code, RFID badge or other wireless beacon.) In this way the number of individuals, and their density in a specific space, can be determined for demonstrating compliance. For example, knowing the number of individuals allowed in a certain area would provide a density value that would act as a threshold in the system. In this way transmission risk can be reduced and compliance can be demonstrated. For example, the mechanism automatically determines if a social distancing threshold has been broken by monitoring distances between two or more proximity beacons worn by individuals. In another example, a proximity technology monitors distances between individuals, tracks and communicates resulting data, and communicates alarms in various ways, in response to threshold distances being breached or a threshold number of individuals being detected in a certain area.

The mechanism may receive and process information from one or more auditing systems for creating audits and capturing data via created audits, wherein an auditing system can be defined as having: one or more storage machines holding instructions executable by one or more logic machines to effect the operations of: creating an audit, presenting the audit to an auditor user, capturing data via an interface of the audit, compiling the data as results, presenting the results, wherein the audit includes audit elements, the audit elements configured to generate a score, wherein the instructions are further executable to categorize generated scores, and wherein the instructions are further executable to determine a location of an auditor device for sending audit content to the auditor device according to the location.

The mechanism may receive and process information from an auditing and performance driving system, wherein the system can be defined as having, one or more storage machines holding instructions executable by one or more logic machines to effect the operations of, from a group of tasks provided by upper management, schedule tasks according to a unique time schedule of an individual facility while obeying restrictions applied by the upper management, delegate one or more of the tasks to one or more employees, to an assignee employee, display one or more steps required to complete the delegated task, receiving an input that indicates that an employee has completed a delegated task, creating an audit for auditing the task, presenting the audit to an auditor user, capturing data via an interface of the audit, compiling the data as results, and presenting the results. Steps could be added in a task along with evidence that these steps are completed. A parent level of a task list could be checked off (evidence completed), and alternatively or additionally, child levels of tasks could be checked off.

The mechanism may be configured to display a dashboard that is updated in real time, according to real-time-updated data streams of various parameters. For example, the mechanism is configured to generate a compliance reading in response to analyzing a plurality of contagion-related parameters continuously updated in real-time. Such a compliance reading could be a score out of 100, for example, where 100 would be perfect compliance (based on all the data streams) and 0 would be the worst. In such a way, the data streams are compiled and presented according to proprietary algorithms, or algorithms suggested by authorities, such that a user can quickly monitor and demonstrate compliance, while the system automatically detects specific problems. For example, very granular issues such as a specific individual (using their ID # or beacon) not wearing a mask or even more overall issues such as a number of people exceeding the allowed limit can be automatically detected to generate an automatic alert. The mechanism can be configured to store and/or access personal details of a passenger, such as personal ID info, health info, passport pages, and travel history.

The mechanism can be configured to read QR codes to determine a volume of people, a sequence/distance between people, execute contact tracing based on a position in queue, and track passenger progress through busses & terminals. It is to be understood that the location could include other locations beyond busses and terminals. For example, this could be expanded to any closed system where a relatively fixed group of people are circulating at random between pre-determined venues, and indoor/outdoor spaces. The people may have agreed to be part of the system upon entering (e.g. checking in or entering an entertainment park hotel (e.g. DISNEY, EPCOTT), boarding a monorail, etc. In other words, the individuals moving through the system could be already known at a certain entry point, while having a specially configured infrastructure to monitor the people within boundaries (e.g. geo-forced boundaries.) Such a QR code could be any appropriate machine readable item without departing from the spirit or scope of this disclosure.

The algorithm may track who was present, where, how far away, and for how long, an encounter occurred. For example, a carrier (e.g. John Smith) was near Mary Jones (unsuspecting victim). Their encounter had 1-2' of range at 8.3 seconds, 2-4' range at 4.2 seconds, and 4-6' range at 3.2 seconds, etc. Each of these proximity ranges would have an associated risk value that would be applied against the duration. The result is a calculation of total exposure risk for a specific encounter. This method would be applied to subsequent encounters of Mary Jones. However, since Mary Jones may not have been deemed infected yet, her subsequent encounters would be treated with less concern (lower risk) as compared to the encounters of John Smith.

The time period that passed since Mary's encounter with John Smith would also impact the algorithm For example, Mary would likely not be contagious immediately following her encounter with John and instead she would be more contagious over time. Therefore the risk of her encounters would increase over time. On the other hand some viruses such as Norovirus can be passed between people even if they are not infected, and even if they never get infected, and in this case, the time sensitivity of the risk parameter might not be present. As such the risk parameters could change according to a suspected virus. Some viruses could have different risk profiles and the system could be adjusted accordingly or automatically in some instances.

When an individual (e.g. Bill) is determined having a certain virus (e.g. Norovirus), the system could determine that Bill was at a certain location (e.g. Handrail) when another individual (Suzy) was also near the handrail within some predetermined time (e.g. minutes) and as such determine that there was a risk of transmission to Suzy. But if the system confirmed that the handrail was actually cleaned properly, then the system could disregard or reduce the chance that Suzy is flagged infected. The degree in which would be adjusted could be according to the confidence of the system's knowledge about the cleaning of the handrail. This confidence could be determined by evaluating past audits/inspections of the same worker's performance on the same task (not just their overall performance).

Therefore the algorithm is used to calculate one or more real-time, continuously updated, risk factors, as well as end-of-the-day risk factors, which would be tailored to most effectively indicate risk based on how and when a contagion is transmitted between people.

Depending on what factors are determined to be involved in a specific contagion of concern, appropriate preventative (pre-determined schedule) and reactive (derived requirement based on conditions) steps would be executed. In other words some contagions may be transferred through surfaces and touch but not through air, and vice-versa. As such different protocols would need to be taken.

For example, with an airborne transmission, HVAC systems (air-handling) are important and their associated filters can curtail transmission. So when a contagion is understood as being capable of airborne transmission, the HVAC systems could be updated and configured accordingly as new information is learned about the contagion. After such modifications (assigned as tasks) are complete, and auditor could be assigned to check the response. This would affect the system's information about the confidence of the completion of a worker's task and ultimately impact the risk factor applied after task completion.

Another way to determine proximity/distance and duration could be through a technology that calculates distances using an algorithm that analyzes a high-definition video footage/live feed of a normal (non-thermal) video/surveillance camera. This is a method, among others, that could be used to track proximity.

The mechanism can be configured to keep track of staff ID #, staff name, department, when an area is cleaned, a name/ID of cleaner, an area and sub-area (location), whether PPE was worn, PPM chemicals detected, whether a sanitizing technique was conducted, the results or execution of swab tests (e.g. 2 or more types), and the execution and/or results of a gel test. Furthermore, the mechanism is configured to gather information from personal proximity beacons and associate such beacons with a passenger name/ID, their area/location, a crew name/ID and/or their location. In this way the mechanism is configured to execute contact tracing by determining a passenger name/ID, their area/location, the contacts they have had (e.g. passenger/crew), the crew or passenger name in contact. It is to be understood that the scope of the tests could be beyond that of those mentioned herein. For example, COVID tests, testing sewage, or other tests could be done to mark the presence of contagion.

Furthermore, for contagion management and containment, the system could determine if chairs/tables are spaced apart properly (social distancing of groups) and determine if face masks are present in storage lockers or dispensers. In detecting exposure to a contagion, the system may determine the duration of exposure. The duration of exposure to a potential carrier could be used in determining risk metrics for individual profiles and contact tracing.

Automatic cleaning and sanitizing may include driving the assignment of tasks based on requirements (e.g. predetermined or dynamically determined.) For example, to-be-audited elements that are likely contributors to a transmission might be given priority for a sanitizing routine. As a non-limiting example, determining that there is a virus present in the ventilation/HVAC could trigger scheduling of a specific task to change an air filter, and when a worker marks this task "done", an audit of that action could be assigned to an auditor.

With respect to demonstrating medical care abilities, essential medical parameters and data is tracked by the mechanism to demonstrate medical care, such as number of patients that are in treatment, and carrying capacity of a medical area.

Relationships between the one or more data streams, or data stores, may be evaluated to determine a level of compliance, represented by one or more numbers or visual representation, or semantic or haptic representations. The data is reported in true real-time (updated continuously), driving the ability for immediate corrective action. The data is reported to indicate compliance with standards, such as the percentage of individuals wearing masks.

A questionnaire may be presented and the outcome of a questionnaire is stored in the system. This data would be stored in the system in relation to the contact tracing mechanism.

The mechanism may automatically schedule next actions according to a detected contagion-related risk condition, such as a nearest worker being assigned to investigate improper mask wearing or being assigned to sanitize a surface. This can be done using an auditing system, or performance driving system, as a non-limiting example.

Compliance may be demonstrated through data gathered on social distancing, contact tracing, rigorous screening protocols, enhanced sanitization measures, and onboard medical care & treatment, continuously, in real time, 24/7, through a terminal, onboard, and for passengers and crew members. A personal details portion of the mechanism captures required personal travel information, a QR code portion triggers and records each step of an individual through an onboarding process (e.g. shuttle bus, transport, terminal check-in). A temperature screening portion executes an active and passive testing of body temperatures in a terminal or onboard, or anything throughout a cruise. An automatic cleaning and sanitizing program is executed on buses, terminals, and onboard, and comprehensively tracked with data. A contact tracing technology traces individuals who have had contact with a person of concern (e.g. possibly infected). Medical care is tracked automatically and monitored via technical systems.

Volume may be determined by automatically tracking a number of QR reads, proximity beacon reads, surveillance camera reads, and people counting devices (e.g. manual). For example shuttle bus capacity can be tracked and controlled automatically, the capacity and flow of checkpoints during embarkation can be restricted. Such tracking and controlling of capacity can be applied to venues and all transit areas, and the individuals can be identified in these processes.

Redundant systems for identifying individuals can be included for additional safety. Such identification can be done even if individuals are wearing masks (e.g. with specialized hardware and software). Any appropriate bio-signatures can be used for such identification (e.g. facial recognition, fingerprint, voice recognition, etc.)

Proximity technology may measure distances between people via a wearable proximity beacon. This beacon can interconnect with the entire system to cross-reference data. Relationships between the beacon and mask wearing can be determined. The beacons can record encounters and the unique IDs of all individuals and/or the beacons can be recorded. Verification of wearing a beacon can be established via various methods. Relative distances between individuals in a queue can be determined, and individuals in a vicinity of a proximity alert can be determined for processing/quarantine if an individual is detected as infected. QR code reads can be sequenced and time between reads can be determined, allowing for one or more individuals to be tracked in their motion and activities.

For tracing contacts, a position in a queue can be determined via QR code scanning to track down people who might have been infected (e.g. individuals in queue next to an infected individual). The proximity beacons can be used for tracing contacts by flagging contacts who have reached a certain proximity with an individual or user. The beacons can be used for people counting. Surveillance cameras can be used for tracing contacts as well as identify the IDs of individuals and identify people who are not wearing masks.

In another example, an overall process can include, as non-limiting examples:

1) Pre-cruise: download the proprietary app, entering required ID details, complete questionnaire, submit photos of passport, and generate QR code.

2) Shuttle bus: record who, how many, and body temperature.

3) Luggage Drop off: Test and Sanitize luggage.

4) Body temperature: temperature gun (Bluetooth), temperature sensing (arch), and temperature reading cameras.

5) Security (Entry): Verify passengers are on manifest for a given cruise, verify ID.

6) Security (X-ray/Temp screening arch): Metal detector Arch, x-ray screening machine.

7) Travel History: Staff examines passport, staff completes questionnaire (e.g. where have you traveled through?), contact history. (Deny or allow boarding).

8) Secondary Medical: actions taken if individual has traveled through certain locations, symptoms are observed by staff (Deny or allow boarding)

9) Proximity beacon (potential combination with RFLD, pre-pair in the mail, or locating this station earlier): receive and pair the Bluetooth beacon wearable, establish IDs to ignore. This step could be moved anywhere earlier in the process to provide a range and duration value to an encounter.

10) Check in process (process varies according to cruise line).

11) Waiting: Terminal (record who, how many).

12) Board ship: record who, how many.

A venue (e.g. restaurant, bar, public area) or transit area (e.g. stairwells, corridors) may include a BG/R Bluetooth Gateway or reader (receiver) which is configured to communicate with a PPB (Personal Proximity Beacon) to determine the proximity of passengers in a specific area (or sub-area) and to count individuals. A volume-control display communicates whether it is OK to enter or when it is not OK to enter according to volume/proximity thresholds. A short range thermal camera and surveillance camera may also be included in such an area. The proximity beacons, or other wearables, could be used to measure and report body temperature.

Body temperature may be constantly and passively measured in venues and transit areas by a thermal camera, where multiple readings are done per person, per day, and analytics are done to ensure a minimum number of readings per day separated by designated periods of time.

A sanitizing and inspecting program may assign and tracks cleaning/sanitizing by unique location and worker, and assigns and tracks auditing and inspection assignments, where inspecting can be done via swab tests and/or gel tests. In another example, staff themselves are inspected (is PPE worn, are correct PPM chemicals used, sanitizing technique).

Swab testing may include, executing a swab test, determining when a surface is cleaned, the name/ID of cleaner, a location or sub-location, an RLU #, and a Pass/Degree of Fail. Gel testing can include executing a gel test, determining if a surface is clean, determining the name/ID of a cleaner, an area/location/subsection, how clean a surface is, and how much time has passed between cleaning. It is to be understood that RLU # could be defined as "Relative Light Unit".

A threshold value (e.g. to signal a possible transmission event), may be dynamic—which could mean that the value changes according to various conditions. For example, one condition that would cause the threshold value to adjust could be an interaction where one person wears a mask while another person is not wearing a mask, both people aren't wearing masks, or both people are wearing masks. This could be dynamically adjusted according to location, or the situation at hand. Further other values could be used to make this dynamic adjustment, such as body temperature or any variable mentioned herein. Furthermore, the above described distance and duration data could be included in this threshold value, which could be dynamic or in some instances not dynamic according to the situation.

A threshold value is adjusted according to location or sub-location in which a possible transmission has occurred. For example, an area with a high density of individuals might have a more sensitive threshold to social distancing, where a more open area may have a greater threshold distance. In other words, the "safe distance" can be adjusted according to a location that the beacon is present in.

Cameras may be used to determine a nature of a violation before an impact on the mechanism's dashboard. For example, in a restaurant it is expected that individuals will be in close proximity to a server while the customers are not wearing masks, so this violation may be disregarded to some extent from impacting the compliance values of the dashboard. For example, the beacon could be informed with such information to disable or adjust at which points the beacon blinks or makes an alert sound or vibrates. In this way the beacons could alert the surroundings or send an alert to the mechanism or an authority. The surveillance cameras can also determine if an employee was doing their job during the violation (e.g. wearing a mask despite the customer not wearing a mask.)

The mechanism may include various devices to ensure health & safety, which may be a negative pressure room or isolation room, and the mechanism tracks and monitors the activity of such devices and whether they are in proper working order.

Body gestures may be monitored and tracked (e.g. via a three-dimensional camera) to identify individuals or determine if the individual is at risk for transmission. For example several coughing or sneezing gestures could be detected to determine that an individual is showing symptoms of infection.

The mechanism may be set up via a kit which includes cameras, computers, beacons, temperature sensors, and/or software. LIDAR and/or infrared can be used instead of Bluetooth for determining proximity between individuals.

In some embodiments the methods, tasks, processes, and/or operations described herein may be automatically effected, executed, actualized, and/or carried out by a computing system including a tangible computer-readable storage medium, also described herein as a storage machine, that holds machine-readable instructions executable by a logic machine (i.e. a processor or programmable control device) to effect, execute, actualize, carry out, provide, implement, perform, and/or enact the above described methods, processes, operations, and/or tasks. When such methods, operations, and/or processes are implemented, the state of the storage machine may be changed to hold different data. For example, the storage machine may include memory devices such as various hard disk drives, CD, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that a certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API). A Global Positioning System (GPS) module could be included in the communication subsystem to communicate location.

As a non-limiting example, the disclosure teaches action by a processor to execute a "determining step" that cannot be done mentally, for example by determining any of the disclosed data, informatic values, or states by automatically tracking other data, informatic values, or states. For example, the disclosed systems and methods may automatically determine a second (dependent) state or value by automatically tracking a first (independent) state or value, the second state automatically depending on the first state.

The disclosure includes the practical application of a processor (logic machine), and this practical application may include the receiving of an input through a graphical user interface (GUI) such as a user selection to execute one or more tasks or operations. Such a practical application may include the automatic operation of one or more data- or state-determining tasks in response to such a user selection or user input. The practical application as such may automatically execute any of the herein operations based on automatically determining any of the disclosed values, data, informatics, or states.

It is to be understood that the disclosed systems and methods provide a specific manner of automatically executing or actualizing the disclosed tasks, operations, or methods in a manner that is an improvement over known systems and solutions. In addition to being a practical application of machines, the disclosure includes an inventive concept that is not anticipated or obvious in view of known systems and methods.

Furthermore, the systems and methods disclosed herein are configured to solve technical problems in computing in the field of the disclosure as set forth in the background section, where the problems have attributes that hinder, limit, and/or prevent the features, aspects, or elements disclosed herein from being enabled and/or implemented. Therefore the disclosed technical solutions eliminate or alleviate these problems and positively contribute to the technical abilities of existing computing systems and methods.

As a non-limiting example of such a practical application, embodiments of the invention may include a system, a method, and/or a computer program product. The computer program product may include a computer readable storage medium (or media) having computer readable program instructions thereon for causing a processor to carry out aspects of the invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on one or more standalone computers, partly on one or more standalone computers, as a stand-alone software package, partly on one or more standalone computers and partly on one or more remote computers, partly on one or more standalone computers and partly on one or more distributed computing environments (such as a cloud environment), partly on one or more remote computers and partly on one or more distributed computing environments, entirely on one or more remote computers or servers, or entirely on one or more distributed computing environments. Standalone computers, remote computers, and distributed computing environments may be connected to each other through any type of network or combination of networks, including local area networks (LANs), wide area networks (WANs), through the Internet (for example using an Internet Service Provider), or the connection may be made to external computers. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the invention.

Aspects of the invention are described herein with reference to schematic flowchart illustrations and/or block diagrams of methods, apparatus (systems), functions, and computer program products according to embodiments of the invention. It will be understood that each block of the flowchart illustrations and/or block diagrams, and combinations of blocks in the flowchart illustrations and/or block diagrams or functions, can be implemented by computer readable program instructions. Functions, including policy functions, are groups of computer readable program instructions grouped together that can be invoked to complete one or more tasks.

These computer readable program instructions may be provided to one or more processors of one or more general purpose computers, special purpose computer, or other programmable data processing apparatus to produce a machine, such that the instructions, which execute via the processors of the one or more computers or other programmable data processing apparatus, create means for implementing the functions/acts specified in the flowchart and/or block diagram block or blocks. These computer readable program instructions may also be stored in one or more computer readable storage mediums that can direct one or more computers, programmable data processing apparatuses, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto one or more computers, other programmable data processing apparatus, or other devices to cause a series of operational steps to be performed on the one or more computers, other programmable apparatuses or other device to produce a computer implemented process, such that the instructions which execute on the computers, other programmable apparatus, or other devices implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In conclusion, disclosed is a mechanism for implementing and demonstrating compliance in accordance with social distancing, contact tracing, screening, and sanitization or any appropriate other task such as mask wearing or other factors contributing to contagion or contagion compliance.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A mechanism for implementing and demonstrating compliance with contagion-related protocols, the mechanism comprising a processor configured for communicating compliance data through a dashboard, wherein the dashboard is configured to receive a plurality of data streams relating to various contagion-related risk parameters;
   wherein the mechanism is configured to store and/or access personal details of a passenger, the details being at least one of personal ID info, health info, passport pages, and travel history;
   wherein the mechanism is configured to read QR codes to determine a volume of people, a sequence/distance between people, execute contact tracing based on a position in queue, and track passenger progress through busses and terminals;
   wherein the mechanism is configured to execute temperature screening and associate the temperature with a passenger name/ID, passenger temperature, crew name/ID, and crew temperature;
   wherein the mechanism is configured to keep track of staff ID #, staff name, department, when an area is cleaned, a name/ID of cleaner, an area and sub-area, whether PPE was worn, PPM chemicals detected, whether a sanitizing technique was conducted, the results or execution of swab tests, and the execution and/or results of a gel test;
   wherein the mechanism is configured to gather information from personal proximity beacons and associate such beacons with a passenger name/ID, their area/location, a crew name/ID and/or their location;
   wherein the mechanism is configured to execute contact tracing by determining a passenger name/ID, their area/location, the contacts they have had, the crew or passenger name in contact;
   wherein relationships between the one or more data streams, or data stores, are evaluated to determine a level of compliance, represented by one or more numbers or visual representations, or semantic or haptic representations;
   wherein data is reported in true real-time, updated continuously, driving the ability for immediate corrective action;
   wherein data is reported to indicate compliance with standards, reporting at least a percentage of individuals wearing masks;
   wherein particulate matter below a threshold is detected using an air quality sensor;
   wherein the mechanism automatically schedules next actions according to a detected contagion-related risk condition, including at least a nearest worker being assigned to investigate improper mask wearing or being assigned to sanitize a surface;
   wherein a QR code portion triggers and records each step of an individual through an onboarding process;
   wherein a proximity technology monitors distances between individuals, tracks and communicates resulting data, and communicates alarms in response to threshold distances being breached or a threshold number of individuals being detected in a certain area;
   wherein IoT sensors are deployed in health and safety appliances;
   wherein body volume is determined by automatically tracking a number of QR reads, proximity beacon reads, surveillance camera reads, and people counting devices;

wherein relationships between the beacon and mask wearing is determined, the beacons recording encounters and the unique IDs of all individuals;

for tracing contacts, a position in a queue is determined via QR code scanning to track down people who might have been infected, wherein the proximity beacons is used for tracing contacts by flagging contacts who have reached a certain proximity with an individual or user, wherein the beacons are used for people counting and surveillance cameras are used for tracing contacts as well as identifying the IDs of individuals and identify people who are not wearing masks;

wherein for temperature screening, data from a hand-held gun or touchless automatic temperature screener are fed into a data stream;

wherein a go/stop signal indicates whether the individual is allowed to proceed passed the checkpoint;

wherein two or more cameras are simultaneously paired to determine temperature, including a thermal imaging camera and a regular surveillance camera;

wherein a venue or transit area includes a BG/R Bluetooth Gateway or reader which is configured to communicate with a personal proximity beacon to determine the proximity of passengers in a specific area and to count individuals; and wherein a volume-control display communicates whether it is OK to enter or when it is not OK to enter according to volume/proximity thresholds.

* * * * *